US011976846B2

(12) United States Patent
Ayesa (10) Patent No.: US 11,976,846 B2
(45) Date of Patent: May 7, 2024

(54) PURE AND NATURAL AIR DISTRIBUTION SYSTEM

(71) Applicant: Rubén Alberto Ayesa, Ciudad Autónoma de Buenos Aires (AR)

(72) Inventor: Rubén Alberto Ayesa, Ciudad Autónoma de Buenos Aires (AR)

(*) Notice: Subject to any disclaimer, the term of this patent is extended or adjusted under 35 U.S.C. 154(b) by 791 days.

(21) Appl. No.: 17/074,447

(22) Filed: Oct. 19, 2020

(65) Prior Publication Data

US 2021/0116137 A1 Apr. 22, 2021

(51) Int. Cl.
*F24F 8/10* (2021.01)
*A61L 9/20* (2006.01)
*F24F 3/14* (2006.01)
*F24F 8/22* (2021.01)

(52) U.S. Cl.
CPC ........ *F24F 8/10* (2021.01); *A61L 9/20* (2013.01); *F24F 3/14* (2013.01); *F24F 8/22* (2021.01)

(58) Field of Classification Search
CPC ........ F24F 8/00; F24F 8/10; F24F 8/20; F24F 8/22; F24F 3/12; F24F 3/14
See application file for complete search history.

(56) References Cited

U.S. PATENT DOCUMENTS

| | | | | |
|---|---|---|---|---|
| 4,147,185 A | * | 4/1979 | Hines | F16L 55/0337 138/143 |
| 4,323,113 A | * | 4/1982 | Troyer | F28D 20/0056 165/45 |
| 8,306,669 B1 | * | 11/2012 | Smith | F24F 11/46 700/202 |
| 2016/0228811 A1 | * | 8/2016 | Meirav | B01D 39/02 |
| 2017/0368490 A1 | * | 12/2017 | Wall | B01D 46/0005 |
| 2018/0356109 A1 | * | 12/2018 | Nomura | F24F 1/00 |

* cited by examiner

*Primary Examiner* — Sean E Conley
*Assistant Examiner* — Justin Hwang
(74) *Attorney, Agent, or Firm* — Defillo & Associates, Inc.; Evelyn A. Defillo (57) ABSTRACT

A purified and natural air distribution network including a number of suction towers that are connected to a secondary duct, which in turn is connected to a main trunk network, in which there are collector units and/or suction that drag the air through the network. The main trunk network air filtering packages and in turn along the extension there is at least one cleaning and filter change station and the main trunk network extends from the plurality of suction towers arranged, for example, in an open space with natural air up to the home facilities that have supply units of the natural air, thus providing a renewable and non-polluting, clean and conditioned supply, beneficial for the health of the user and the environment.

5 Claims, 13 Drawing Sheets

PURE AND NATURAL AIR DISTRIBUTION SYSTEM

1. FIELD OF THE INVENTION

The present invention relates to a pure and natural air distribution system and relates to the field of devices, apparatus, and arrangements employed for the collection, purification, and conveyance of fluids through distribution network; more particularly the invention is related to distribution networks such as water distribution, gas distribution, electricity distribution, or among others.

2. DESCRIPTION OF THE PRIOR ART

The present invention is related to the current state of the art in fluid handling for the general benefit of a population, and the complication caused to the environment by current air pollution.

Consumption, as a concept, in modern society pollutes the air, therefore, industry, factories, all combustion gases, heating and cooling, are the origin of atmospheric pollution that potentially affects society and the planet, in its direct relationship with life quality.

Currently there are distribution or supply networks that are used to provide gas, oil, water and electricity, where these networks are essential for the development of modern life, since users do not have to have containers or means of accumulation of energy such as gas "carafes", an electricity generator set or a number of batteries connected to a power generating motor, wherein said energy accumulation means supply the home in a short period of time.

Therefore, the distribution network of such energy sources makes it easier for users to use them, since only by connecting to the network they obtain the benefits of them. But the energy distribution networks or energy sources, such as gas or electricity, present an exclusive problem that is global warming, since these sources, to give an example, pollute and heat the planet, both due to the emanations of said gas emitted. by stoves or as the ambient air that is heated in proportion by air conditioners that are currently in most homes, businesses, businesses or the like and run on electricity.

The energies or energy sources are not renewable, that is, they leave residues that cause pollution to the environment, their consumption causes the reserves of both water or gas to be depleted, in many cases causing the loss of water, where its cycle It is of natural purification is very slow, and others, such as oil that are exhausted leaving residues.

The objective would be to have a renewable source or renewable natural resource that does not pollute and that helps to improve the environment, allowing, in turn, the ideal conditioning for the development of human beings in adverse conditions, according to their convenience, as well as that said resource is provided through a distribution network to all users.

BRIEF DESCRIPTION OF THE INVENTION

It is an object of the present invention to provide a pure and natural Air Distribution System, which enables air to be delivered from one place to another through a network, where they include as suction means towers strategically positioned in places of choice and also That said provision improves the environment by helping to reduce, gradually and constantly, air pollution.

It is also another object of the present invention to provide a trunk arrangement for the distribution of pure and natural air, wherein said arrangement comprises a number of suction towers that are connected to a main trunk network, in which there are forcing units and/or of suction, including air filtering packets in said network, with cleaning and changing stations, strategically placed. The mentioned main network extends from suction towers conveniently arranged, for example in an open space, to residential facilities that have supply units of said pure and natural air, thus providing a renewable and uncontaminated fluid prepared for human consumption.

It is also another object of the present invention to provide a trunk air distribution arrangement that includes suction means through existing devices fed with pure energy, generated with external devices of wind and solar origin, natural that allow the energy sustainability of the system.

It is still another object of the present invention to provide an arrangement of conduits that allows the transfer of air from its extraction origin, in its natural state, so that it maintains a temperature, being able to be purified by filters that remove unwanted particles or elements and/or already contaminated.

It is therefore an object of the present invention to provide a distribution network of pure and natural air, through air suction towers, connected to at least one duct that in turn connects to said network and a unit of supply arranged in at least one enclosure within which said air is distributed, air forcing units in said backbone network and air suction units in said supply units, including in at least said network filter packets devices.

Still other objects of the exemplary forms of the present invention will become apparent from the detailed description of the invention section and from the appended claims.

BRIEF DESCRIPTION OF THE DRAWINGS

To clarify the object of the present invention it has been illustrated in different figures.

DETAILED DESCRIPTION OF THE INVENTION

The numerical references involved in the figures are:
Rtp: Main transport backbone.
R: Fluid network.
dt: From the hopper.
ac: Access to the pipeline.
rau: Urban supply network.
Sa: Air suction.
1. Suction hopper.
2. Node connecting piece for secondary ducts.
3. Secondary ducts.
4. Main duct.
5. Mounting flange and coupling.
6. Primary fluid conduit.
7. Secondary interconnecting line.
8. Air suction Tower.
9. Flexible connection.
10. PVC conduit.
11. Structural ribs.
12. Flexible conduit.
13. Zinc sheet.
14. Ultraviolet light device.
15. Water trap.
16. Air chamber.
17. Access platform.
18. Intake grille.
19. Winch.
20. Elastic anchorage.
21. Pipe duct section.
22. Turbine.
23. Support.
24. Turbine shaft.
25. Motor.
26. Ultraviolet (UV) device for air disinfection and asepsis. 27.
27. Fixing means.
28. Connecting cable.
29. Video camera.
30. Sanitary sensor.
31. Ultraviolet lights.
32. Filter holder.
33. Filter.
34. Stainless steel mesh.
35. Activated carbon core.
36. Polyurethane core.
37. Concrete base.
38. Articulation.
39. Humidifying sprinkler.
40. Louvre damper.
41. Female connection.
42. Flexible duct 90° connection.
43. Flexible conduit.
44. Lower connection piece.
45. Paper core filter of the air filter packets.
46. Filter with polyurethane core of the air filter packets.
47. Drainage device.
48. Upper connection piece.
49. Sewer manhole.
50. Water trap.
51. Inspection ladder.
52. Pedestrian access.
53. Concrete structure.
54. Stainless steel sheet.
55. Air suction.
56. High density vinyl material.
57. Vertical piping.
58. Secondary ducting.

The air extraction is carried out by means of suction hoppers strategically placed on the ground where the air is extracted. (FIG. 3b)

Figure 3A:
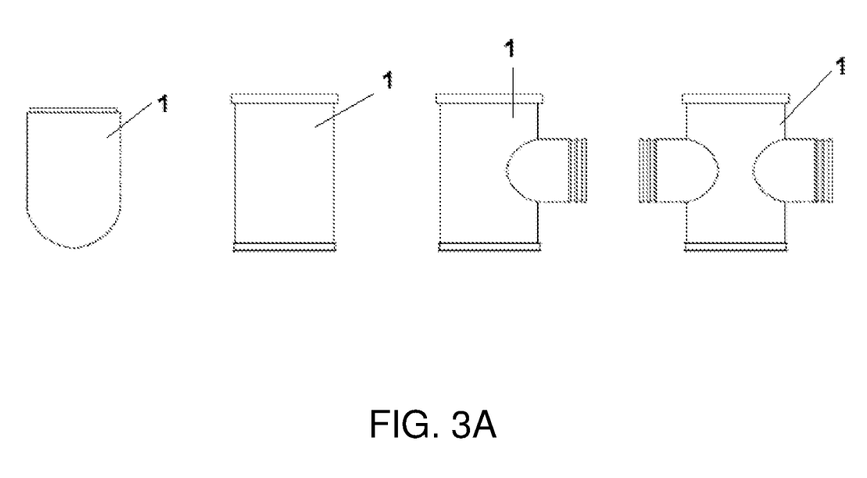
FIG. 3A are plan views of duct types and ends.
Figure 3B:
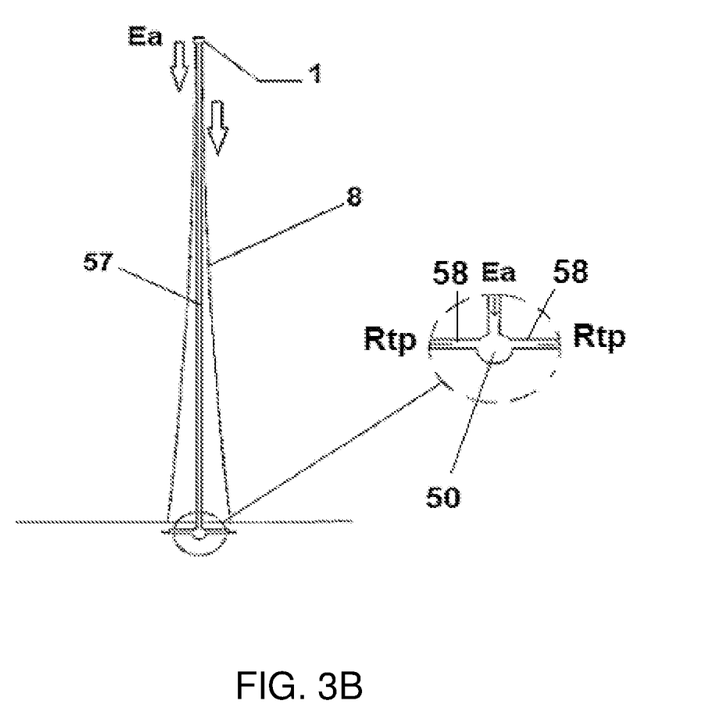
FIG. 3B is a view of the hopper.

They are made of resistant material composed by prefabricated pieces by means of conduits that are connected to them and through an overhead wire system which is connected to the primitive net (FIG. 3)

Figure 1:
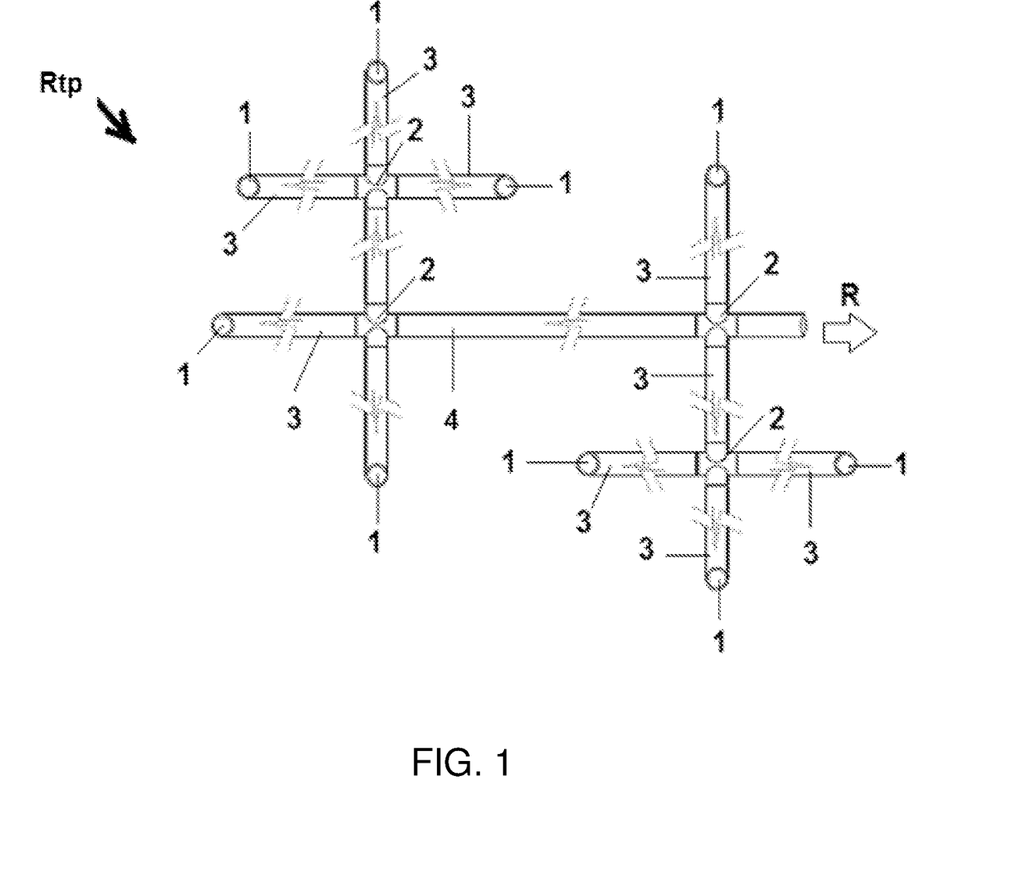
FIG. 1 is a plan view wherein the air removal is made through a hopper strategically located on the field where it is carried out.
Figure 2:
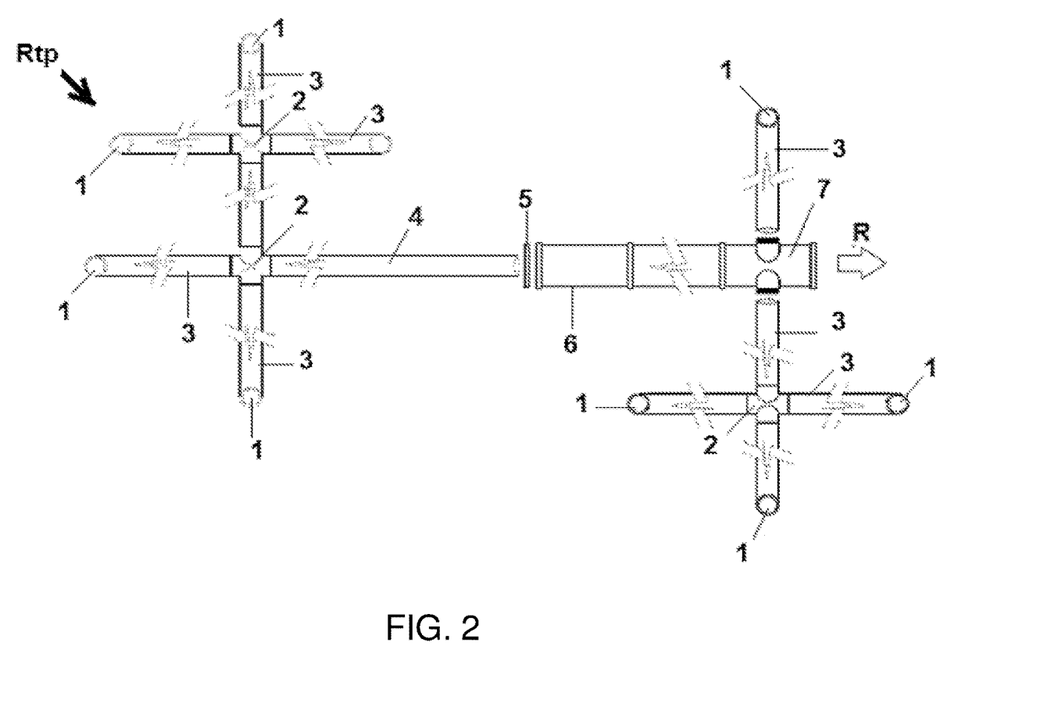
FIG. 2 is a plan view wherein the ducts allow the interconnection of suction and expulsion hoppers along the length and width of the line in question, it is only carried out by means of different connection pieces designed for this purpose that structurally allow all the connection variants in the four cardinal points, multiplying in progression arithmetic in every way.

The suction hoppers are make up a suction system as well as an expulsion system, for the first there is in the highest part of the tower, the first filter of the entire system composed of a woven steel mesh that allows taking the air free of unwanted elements, for the second there is no specification other than the above, to In turn, the tower continues below the primary conduits for conducting the fluid, ending in a water trap and/or unwanted elements (sand), which by means of a pump are expelled at ground level and returned to the environment (according to FIG. 1).

The accesses to them are made at level, through safety gates, which allows the duct network to be checked and inspect, as well as the access to the pumping well that acts as a trap for liquids and unwanted elements.

Hoppers details are shown in FIG. 3b.

Figure 4:
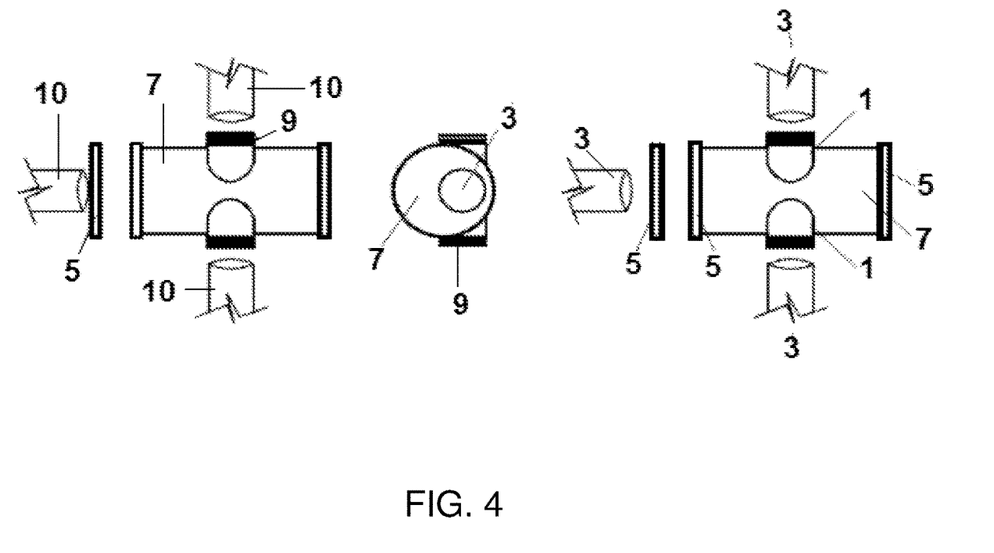
FIG. 4 are views of the connection of the primary conduits with the primary network is made with a piece designed for this purpose with the particularity of mechanical assembly, without welds, which allow clamping and stability by means of a winch clamp system with steel cables, and mordant built with recycling tires.
Figure 5:
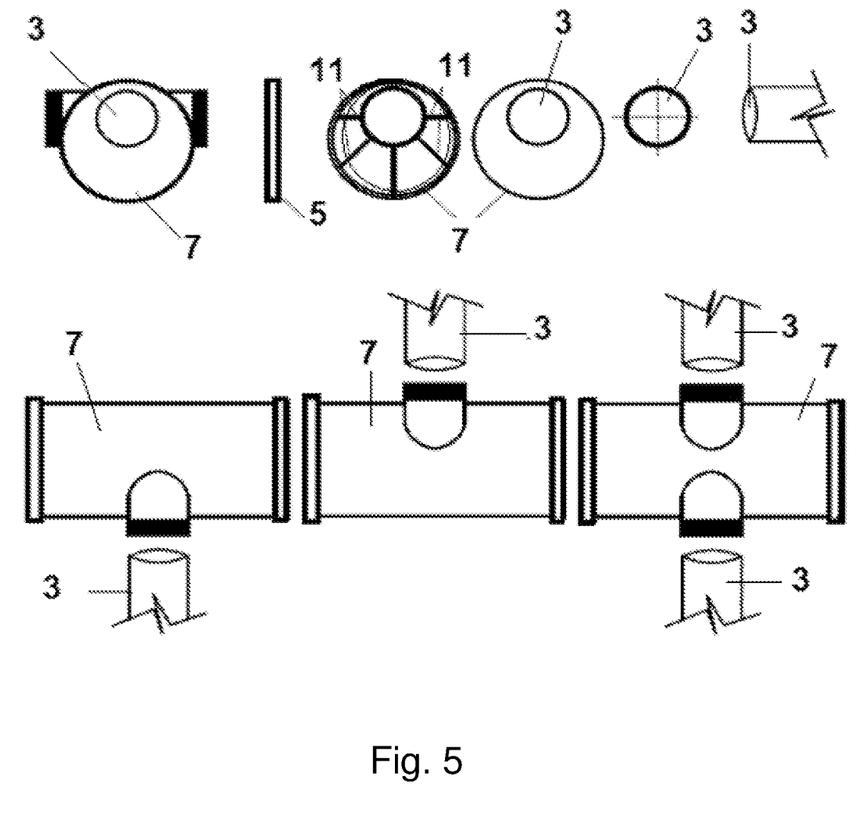
FIG. 5 are views of the connection of the primary conduits with the primary network is made with a piece designed for this purpose with the particularity of mechanical assembly, without welds, which allow clamping and stability by means of a winch clamp system with steel cables, and mordant built with recycling tires.

The ducts allow the interconnection of suction and expulsion hoppers along the length and width of the line in question, it is only carried out by means of different connection pieces designed for this purpose that structurally allow all the connection variants in the four cardinal points, multiplying in progression arithmetic in every way. (FIGS. 3 and 4)

The ducts are built in the same material as the hoppers, with the variants in reinforced plastic, with male and female connection. (FIG. 3A)

Figure 6:
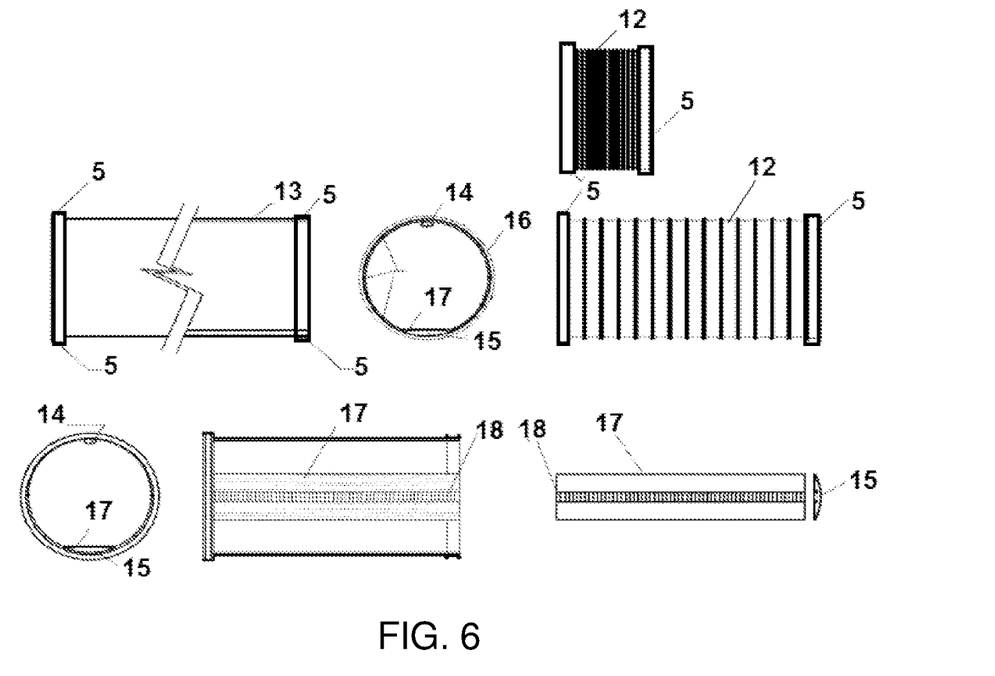
FIG. 6 are view illustrating the agile assembly as well as the easy and clean replacement, (if any), of any of its sections, in turn its interior is composed of an air chamber, no larger than 2 cm, (idem GT expanded polystyrene), between the material of the exterior pipe and the interior zinc sheet finish, which allows the necessary thermal insulation, since the entire network can be semi-buried, buried or level, but always covered with earth, which will allow insulation FIG. 7 are plan views illustrate the ducts, within the primary network, to integrate to the same network, new suction and/or expulsion hoppers allowing the versatility of changes and/or supports not foreseen in their route, for their better performance.
Figure 7:
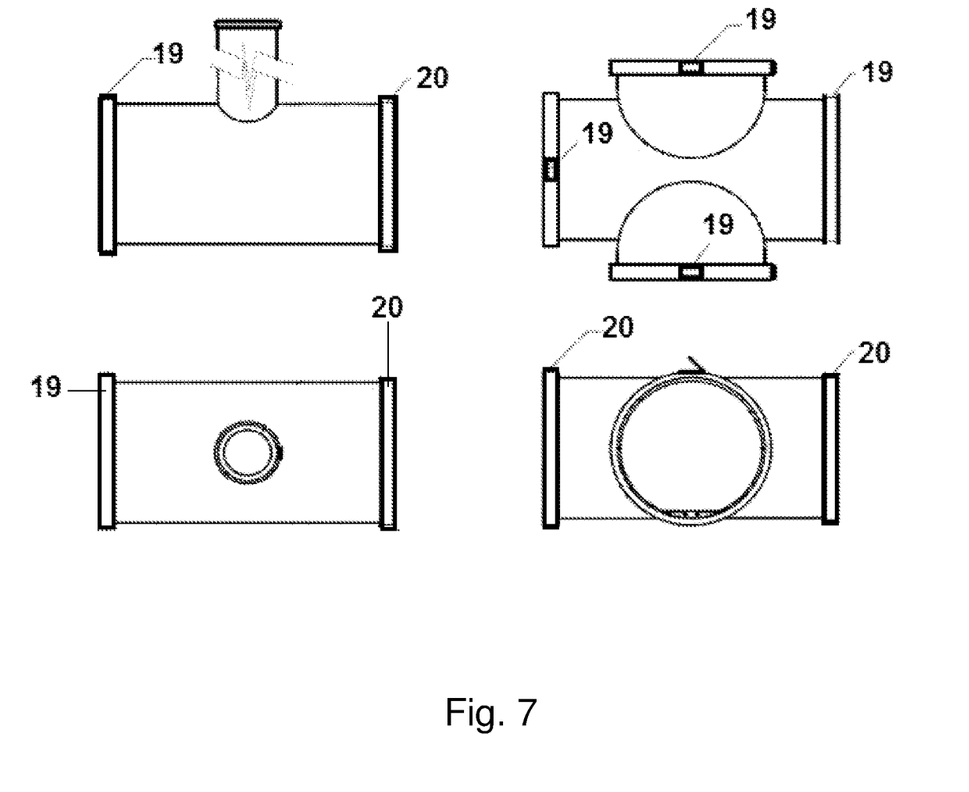

The connection of the primary conduits with the primary network is made with a piece designed for this purpose with the particularity of mechanical assembly, without welds, which allow clamping and stability by means of a winch clamp system with steel cables, and mordant built with recycling tires. (FIGS. 6 and 7)

Figure 8:
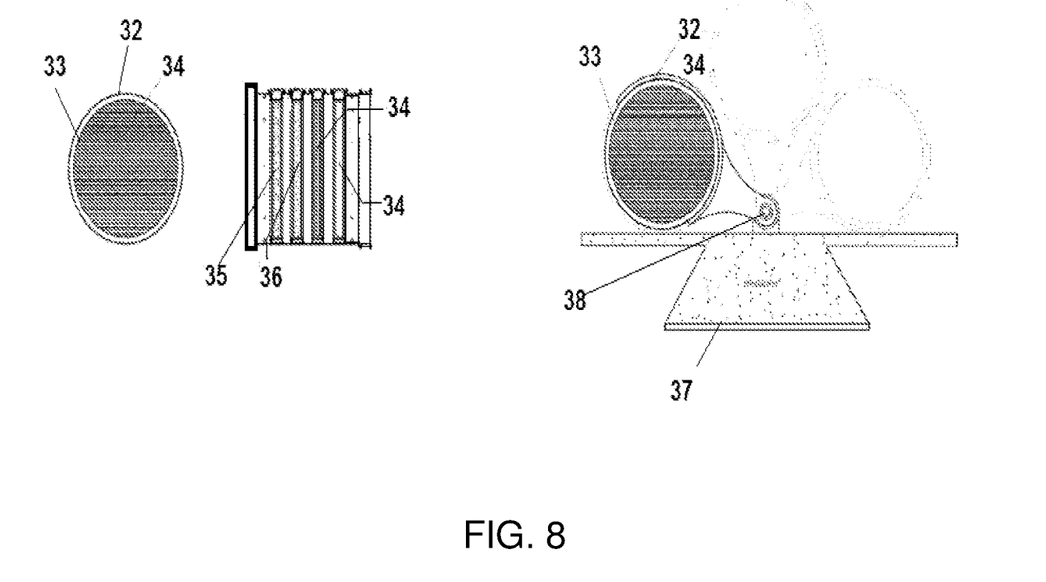
FIG. 8 are views illustrating the system can work for one direction as well as for the opposite; the drag system is composed of a motor, electric, variable power suction reversible twist.

This allows the agile assembly as well as the easy and clean replacement, (if any), of any of its sections, in turn its interior is composed of an air chamber, no larger than 2 cm, (idem GT expanded polystyrene), between the material of the exterior pipe and the interior zinc sheet finish, which allows the necessary thermal insulation, since the entire network can be semi-buried, buried or level, but always covered with earth, which will allow insulation (FIG. 8)

Figure 9:
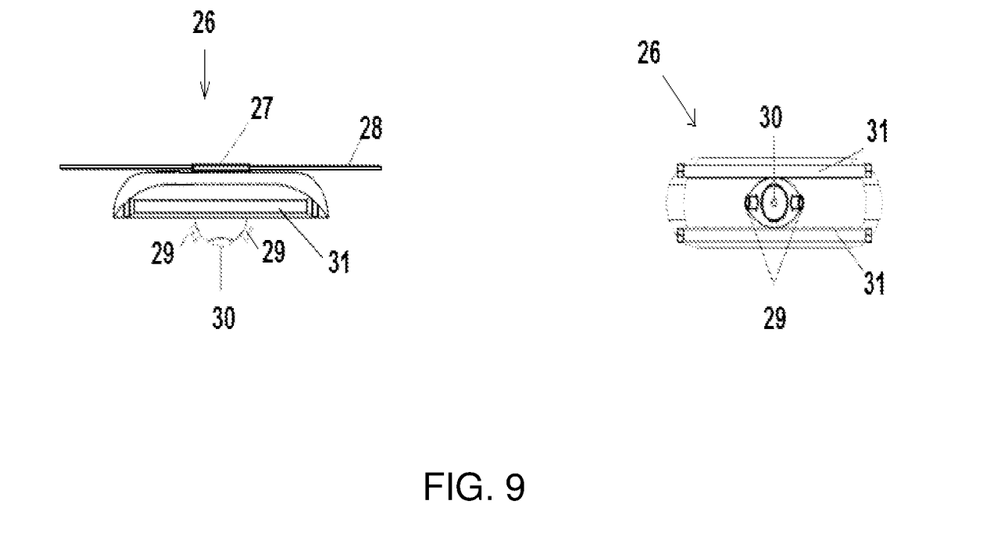
FIG. 9 are plan and elevation views illustrating the sensors of air quality, UV lamps, disinfection and asepsis, image inspection cameras.

Establishing that the comfort standards are between 20° and 22° C., this taking into account that the speed of the fluid will depend on the consumption and/or number of recipients, which makes the regulatory framework of temperature, to reach the desired standards, it is less of a problem, depending on the temperature at the starting point and its path to the distribution point, a thermal gradient calculation, not having too much influence on the whole given that the air supply is always slow, progressive, and constant, subject to the purging system, facilitating any imperfection in the distribution and supply temperature. (FIG. 9)

It is also contemplated and designed for this purpose, the ducts, within the primary network, to integrate to the same network, new suction and/or expulsion hoppers allowing the versatility of changes and/or supports not foreseen in their route, for their better performance. (FIG. 7)

Figure 10:
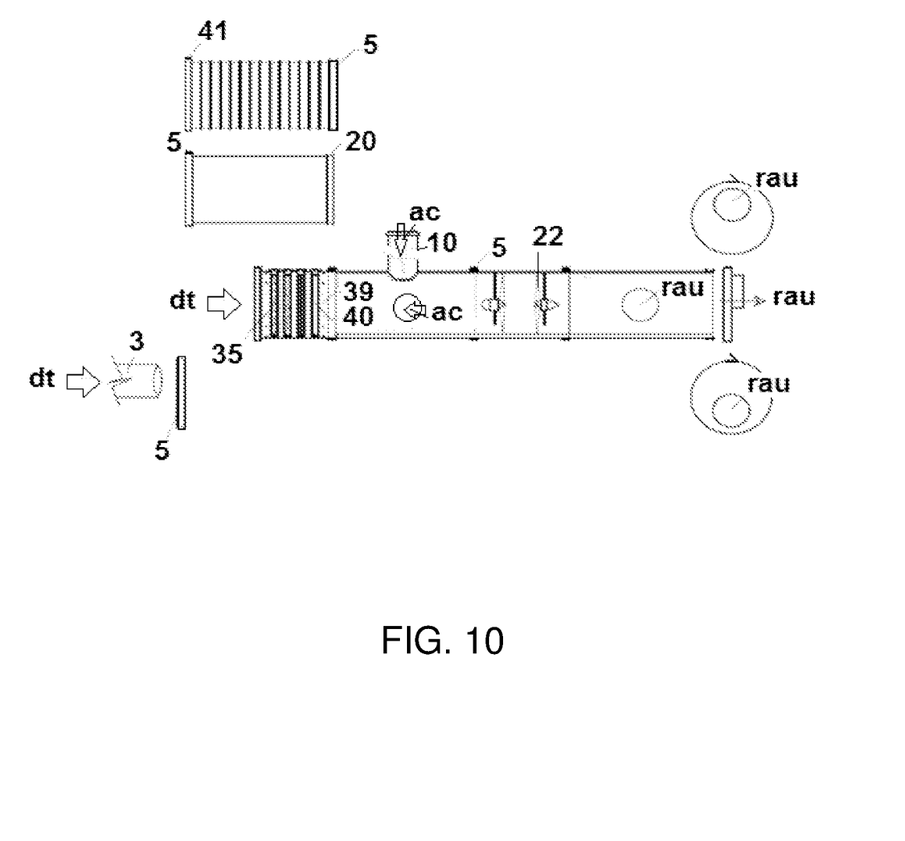
FIG. 10 are plan views of how the circuit is completed with household connection pieces which are assembled to the ducts by means of the cut between ring and ring, assembling by proximity and hooking the piece in question.

The system is open, what does this mean? It means that the system can work for one direction as well as for the opposite. As a result of this, is that the drag system is composed of a motor, electric, variable power suction reversible twist. (FIG. 10)

Figure 11:
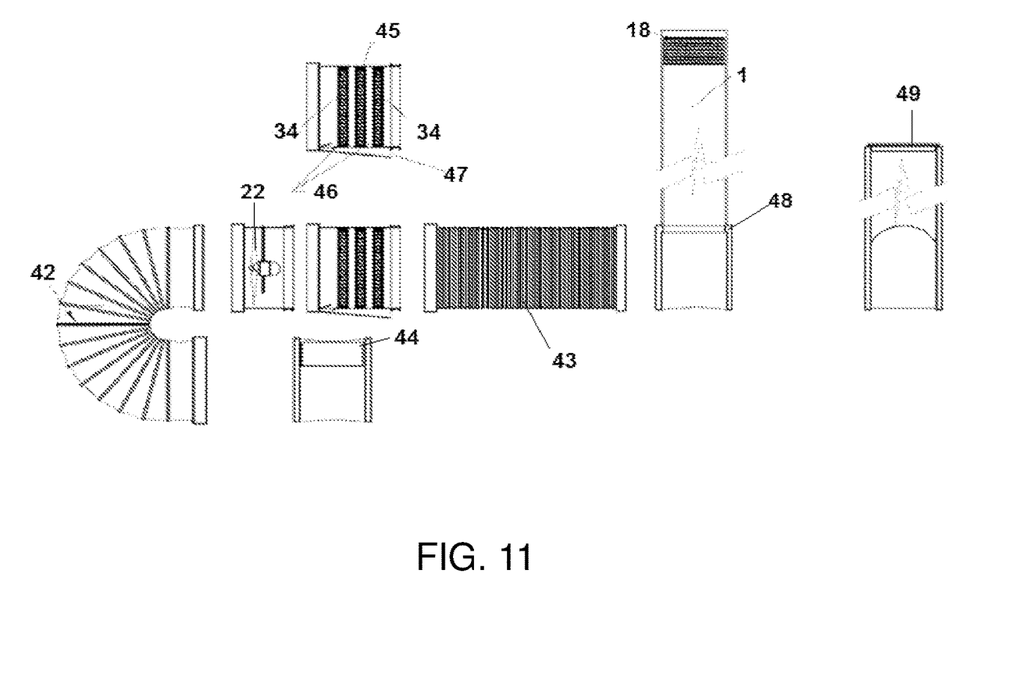
FIG. 11 are plan views illustrating a closed system of a particular climate channeler, making its use something particular in reference to producing specific effects, such as cleaning the air of all water saturation, being in presence of an anti-fog system for motorways and airports
Figure 12:
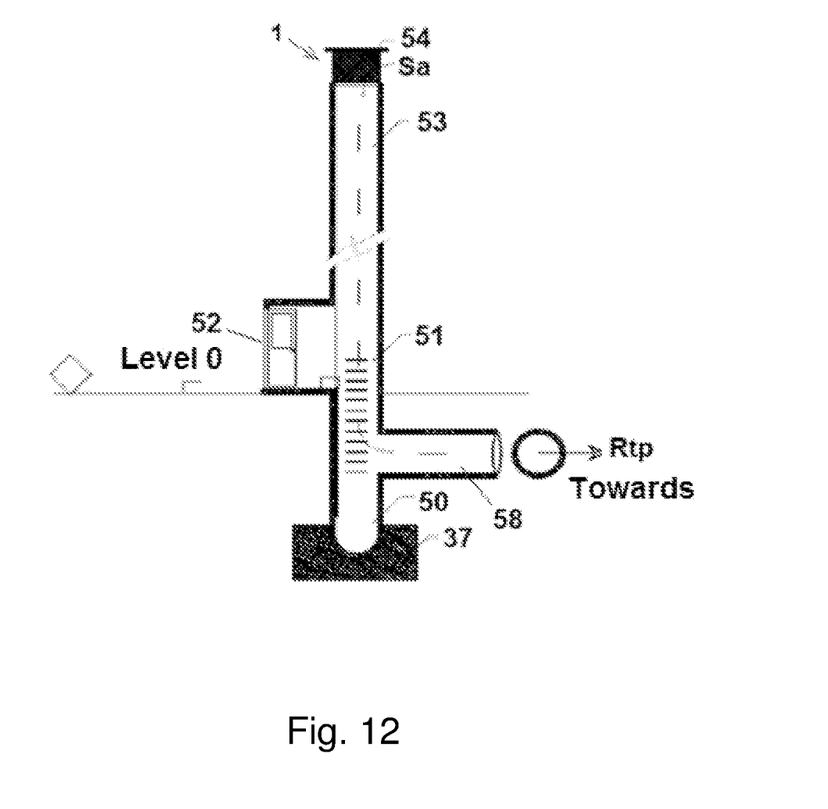
FIG. 12 is an elevation view wherein an artificial wind tunnel is generated, contributing to the consumption of electrical energy that the system demands in the UV devices for disinfection and asepsis of the air.

The circulator is accompanied in its proximity by a wind generator (FIG. 8), thus taking advantage of the artificial wind tunnel generated, contributing to the consumption of electrical energy that the system demands in the UV devices for disinfection and asepsis of the air, as well as image sensors and inspection cameras. (FIG. 11)

Also, on the other hand, the cleaning and filter change stations would also require demand energy which could be provided by the wind generators of the system, we are talking about change station and filter cleaning, these are found in the primary network in order to improve and deliver a basically clean air quality free of any pollutant, with the corresponding oxygen levels through ozonation, delivering air with adequate humidity levels to the different requirements, according to the different climates and seasons of the year. (FIG. 8)

The system contemplates a purging and/or priming of the network, by means of the start-up of the suckers, and releasing the drag air by means of hoppers for this purpose, they will be connected to the primary network by means of a part the same as the fluid distribution, but with the characteristic of the main pipe shutter.

The operation of the system is then composed of the suction and expulsion hoppers, the primary ducts, the primary net, the net drag systems, the home drag systems, the filters, the cleaning and replacement station, the sensors of air quality, UV lamps, disinfection and asepsis, image inspection cameras, ozonators and humidifiers. (FIG. 9)

The urban distribution will be carried out by means of flexible conduits of the order with the particularity of saving space in transport and time in its execution.

The laying is carried out with the current provisions for the laying of services, with the particularity of the creation of cleaning and filter replacement stations, as well as there are currently inspection and treatment stations and chambers for other services. The circuit is completed with household connection pieces which are assembled to the ducts by means of the cut between ring and ring, assembling by proximity and hooking the piece in question. (FIG. 10).

The urban hoppers will be strategically located for the suction of stale air with the intention of sending it to the network, this may be due to peripheral urban implantation, or strategically located within the urban fabric, for its subsequent treatment and its return to the supply network.

Basically, the system is a provider of climates, with the consequent benefits previously stated in another section, of the ecological order, cleaning and air treatment with the consequent benefits for health, on the other hand the system is a channelizer and conductor of climates with the particularity of being able to transfer climatic conditions from one point to another, consequently, it could become a reliever of extreme climatic agents, which through the system will be able to reduce the intensity of the phenomenon, thus reducing the damage that it could cause.

Attentive to the same principle, but already making it a closed system, we are facing a particular climate channeler, making its use something particular in reference to producing specific effects, such as cleaning the air of all water saturation, being in presence of an anti-fog system for motorways and airports (FIG. 11)

The suction or capture of said natural air that runs through said backbone is through at least a number of air suction towers, all connected to at least one duct, which in turn connects to said backbone. The connection of said towers and conduits is made through precast reinforced concrete tubular sections, with end inserts, although said tubular sections could be made of reinforced plastic material, with male and female connections. The number of towers is preferably strategically located, in which the natural air is suctioned in order to take in the air from all the cardinal points. It is worth noting that said number of suction towers can also function for the expulsion of air taken from areas or sectors that must be purified, and as a purge of the system.

The mentioned plurality of towers preferably has, or is composed of, a first air purifying filter which is preferably located on top of a vertical pipe. Said filter is a preferably woven stainless steel wire mesh, and in turn said vertical pipe includes a bottom collecting liquids and waste to which a bilge pump is connected to extract them and their disposal at ground or surface level. The number of suction or expulsion towers have the same access doors for maintenance, which are preferably at ground level and allow entry to the bottom of the tower via stairs, with access to the inspection of the ducts. Said natural air is sucked in as indicated by the arrows EA with the hollow points in FIG. 3B, traveling through the vertical pipe to the connection of the towers, with said duct located above said waste collection bottom supported on a concrete surface.

Although it has been mentioned that the towers are distributed according to catchment coinciding with the 4 cardinal points for the extraction or intake of air, these could be along the length and width of the network, that is, having the suction towers where require. The secondary ducts allow the connection of the system, through a set of connection pieces that allow the placement or structural assembly to capture air at all the required points, preferably multiplying in an arithmetic progression in all directions, where the secondary ducts and the backbone network comprise rigid and flexible pipe sections.

The mentioned set of connection pieces are mounted linearly or jointly to said trunk network by means of assembly and coupling flanges. The connection set is divided into several pieces as illustrated in FIG. 4, where one is a rigid tubular conduit with two connection inlets or outlets that allows connecting two secondary conduits and another piece, or a variant of said set of connecting pieces. connection, is a rigid tubular conduit with a connection inlet that allows connection to a secondary conduit, being able to vary the position or direction of entry or exit, that is, for the direction in which the conduit needs to be mounted. It is worth noting that these flanges will be available where the user requires them for the extension of the main trunk network or secondary conduits.

The set of connection pieces illustrated in FIG. 4 presents an example of the connection of the assembly and coupling flange which, in addition to assembling the ducts to the trunk network, assembles the secondary duct from the number of towers, the tubular duct of the trunk network or main conduit and said flange includes structural reinforcement means. Although the conduits have been illustrated as rigid they could be flexible.

The tubular conduits could also have flexible connection means at the inlets or outlets, with which said set of connection pieces allow an agile assembly as well as an easy replacement of its components if necessary.

For the purposes of the present invention, the ducts that are part of the main network or ducts, allow, if necessary, to integrate new suction and/or expulsion towers that could be incorporated into the main network to provide support to the distribution of natural air and/or purged from the network.

Continuing with the aforementioned, the trunk network or main conduit preferably has sections of rigid conduits, where a section of the conduit that makes up said trunk network is a rigid conduit that includes at one end a flange to anchoring winch and clamping with rubber gasket used on the car wheel used at the opposite end allowing an elastic anchoring that could preferably comprise a winch clamp with steel cables, and a clamp built with recycling tires, preferably selected from a rubber tire. car. These anchoring means allow easy assembly between the conduits that make up said trunk network. In turn, the duct can include a thermal insulator to isolate the air extracted or sucked from the environment and allow the air to pass through in its natural state, thus, the outer part or outer diameter has a suitable material, for example metals, plastics, etc. and the internal diameter of the duct has a preferably "zinc" sheet, but between said external and internal diameter there is an air chamber that preferably is not greater than two centimeters, thus facilitating correct insulation and a plurality of guides of reinforcement. However, the network must preferably be covered with earth for its correct isolation and conservation of the air in its state closest to its required temperatures, therefore said network is preferably underground to obtain better thermal insulation. The supply speed is also a thermal regulator.

The conduit or section of rigid pipe has an access platform and in the center of the access platform there is a cleaning grid corresponding to a water trap for maintaining the distribution network.

Also, the mentioned backbone network presents sections of flexible pipes that comprise flexible conduits illustrated in FIG. 10, which include a number of rings preferably made of steel and joined together by a flexible steel mesh in vinyl or similar termination. Furthermore, the mentioned conduit or section of flexible pipe has, at one end, a "male" connection and, at the opposite end, a "female" connection. Both sections or conduits have said water trap in the lower part or floor for the collection of waste or unwanted elements such as grains of sand, dust, water, or those necessary purification things for proper operation. In the upper part of said ducts and throughout the distribution network there are air purifying means which could comprise lamps or ultraviolet light tubes for disinfection and asepsis for the purification of the fluid, or air filter wire meshes such as it has been previously detailed on the top of the extraction or expulsion towers.

However, the trunk arrangement/disposition for the distribution of pure and natural air, and according to the present invention, includes forcing and sucking units of air mounted in the main trunk network by means of said anchors. For the purposes of the present invention, the forcing/suction units contain the same components, where the forcing and sucking units are arranged to suck the air from the suction towers and help transport the air through the entire backbone. In turn, said units are generally found in at least one of said rigid conduits or sections. In particular, the units will be arranged according to the needs of the network, that is, it will depend on the consumption of home users (buildings or houses) or manufacturing sites and the laying or extension of the present trunk arrangement for natural air distribution.

As mentioned, the air forcing units are located in at least one rigid duct or section, and said units are defined by a fan or turbine of variable power and preferably reversible rotation, to guarantee that the present backbone can operate in both directions, that is, sucking or expelling air through the outer towers. The mentioned fastening turbines or fans are included some fastening elements that are fixed to said trunk duct.

In addition, the disinfection tubes are linked to a sanitary air quality sensor and a video camera, both comprising a disinfection and asepsis device contained within a housing and linked to the secondary ducts 4 or to the main backbone 2.

In spite of the fact that the entire network has filtering or purifying means of the natural air that is transported in said network to residential or manufacturing facilities, filter packets are provided in the present backbone network, better illustrated in FIG. 11 that comprise at least minus a woven stainless steel wire mesh, an activated carbon core, an inert polyurethane core, a toilet paper core, and a duct shutter gate, as well as humidification sprinklers, all arranged side by side. Of course, all or some of these filter elements can be combined depending on the conditions of the air transported. Said filter packets are preferably arranged in a filter change and cleaning station, and these are located in the backbone in order to improve and deliver a basically pure, clean air quality free of any pollutant, with oxygen levels corresponding through ozonation of the same, delivering an air with adequate humidity levels to the different requirements, that is, according to the different climates and seasons of the year. In this way, the filter change stations 51 have a filter carrier or filter pack structure and above said structure and surrounding it there is a closing and holding ring for filters or filter packs and attached to said ring is an arm pivoting that is attached at a distal end of said ring to an anchor arranged in the ground or surface Therefore, through the plurality of suction towers that are for example in a natural forest, the air is sucked and through the secondary ducts, the air travels through said ducts to the main network, which presents the packets of necessary filters, a forcing unit and the power generating turbine and their connections to secondary ducts or access ducts as illustrated in the figures The trunk network crosses and extends, according to needs and calculation, until it reaches urban facilities, where distribution begins through flexible conduits to save space in transport and time in its execution. The laying is carried out with the current provisions of the laying of services.

The air distribution disposition is completed with household connection pieces (connectors) that are assembled to the trunk network, which includes or is made up of the smaller diameter flexible ducts that are the ones that make up the home network. These will go through each block and will be able to form the grids of the apples by means of the connectors. By cutting between hoop and hoop of the duct and assembling by proximity and hooking a piece of home connection, such as the one illustrated above, urban units could present suckers attentive to basic principles of physics, which help the conduction of natural air and enriched by said trunk distribution of air, pure and natural.

The trunk distribution of pure natural air provides the user when breathing processed and purified air, a careful quality of oxygenation, coming from ozonation, with the evident improvement in the quality of life.

After the present invention has been detailed, reference will be made to the advantages provided by the present provision, where it has the particularity of making use of natural air, completing a 100% renewable cycle, which constitutes an inexhaustible and even more, renewable, in order to constantly reuse, thus creating a continuous purification platform, in the constant treatment and filtering of the air.

The natural fresh air distribution backbone arrangement is a provider of climates, with the mentioned benefits of ecological order, cleaning and air treatment with consequent health benefits and sanitation. On the other hand, this provision is a channelizer and conductor of climates with the particularity of being able to transfer climatic conditions from one point to another, consequently it could become a reliever of extreme climatic agents, which through the system will be able to subtract intensity to the phenomenon, thus reducing the damage that it could cause. Attentive to the same principle, but already making it a closed system, you are facing a particular climate channel, making its use somewhat different in reference to producing specific effects, such as the extraction of moisture that the air may have, being in the presence of an anti-fog system for highways and airports. Thus, the arrangement of suction towers along stretches of roads and runways can capture the fog, process the air and facilitate visibility and circulation.

The object of the present invention is to contemplate the use of the terrestrial climate, in order to benefit from the existing temperatures in the different periods and places, with the intention of creating a network, and in this way to be able to channel it to different urban points for its benefit.

On the other hand, and in the face of the aforementioned, the substantial and gradual contribution of environmental decontamination emerges that would diametrically change the current reality of constant and generalized pollution, with all kinds of gas emanations, toxic pollution from the burning of hydrocarbons, in the use daily and widespread fossil fuels, which cause progressive damage to the different layers of our atmosphere, on the other hand, the use and the totally natural and ecological procedure of the invention considers the treatment and filtering of the fluid with the consequent constant purification of the air, producing the gradual disappearance of harmful and destructive pollutants from our atmosphere and from our health.

Also, the use of this provision with its benefits of the speed of natural air transport and its operation at slow or fast speed and beyond the benefits already stated of natural air conditioning in adverse conditions, the suction of strategically located towers, they would easily contribute to the deviation or reduction of certain climatic phenomena that in many cases cause major disasters as mentioned in the previous art. The export and import of climates seems feasible, with the consequent benefit, (and scientific supervision), of bringing humidity to dry climates, with the intention of generating more productive land, humidity to cold climates contributing to the generation of recovery of snowfalls that would produce more ice with the intention of rescuing the ice from global warming, thus generating the natural and consequent benefit of restoring terrestrial climate conditions for the benefit of all.

The operation of this provision contemplates many options for action, all of them beneficial; One of them is the actuation of the trunk arrangement for the distribution of pure and natural air, both in a closed or open circuit, depending on the circumstances, becoming powerful tools to naturally combat phenomena such as fog on highways and airports, creating systems both aerial and underground, depending on whether it is for highways and/or airports.

The present invention produces beneficial habits changes, to the point of generating highly significant savings in consumption, of certain fluids, such as gas, and other derivatives of hydrocarbons, which are consumed with the intention of generating heat, as well as a Substantial savings in electrical energy, used as an alternative to hydrocarbons to drive devices that provide environmental comfort in adverse conditions. This occurs given that the provision of the fluid in comfortable environmental conditions will eliminate boilers and/or air equipment, which artificially supply the fluid, rescuing the atmosphere from emanations that increase global warming as well as pollution from the burning of fossil fuels.

Other advantages that can be mentioned are air purification, generation of comfort with natural and ecological methods, regeneration in the export and import of climates, ice and productive lands, environmental decontamination, generating, in its diversification and activation, generalized conditions for the entire world, gradual return to environmental temperatures consistent with a healthy planet, based on the balance of temperatures by natural means.

What is claimed is:

1. A system for distributing pure and natural air, comprising:
    a plurality of air suction towers located in an open space, the plurality of air suction towers are distributed on the open space according to the four cardinal points, each one of the air suction towers including:
    a vertical pipe located inside of the air suction towers, the vertical pipe including a trap;
    a suction hopper for air intake and air discharge, the suction hopper is located on an upper end of the air suction tower; wherein the vertical pipe is connected to the suction hopper;
    a secondary duct located on a lower side of the vertical pipe, wherein the secondary duct is connected to a collection trap;
    a main trunk network including air filter packets;
    a cleaning station connected to the main trunk network, the cleaning station including an ultraviolet light tube, air quality sensors, and cameras;
    wherein the suction hopper includes a filter holder containing a filter and a stainless-steel mesh;
    wherein the air suction lowers suction air and send the air to the main trunk network, the air is then purified by the cleaning station to obtain purified air, the main trunk network sends the purified air to an urban facility to distribute the purified air into an existing residential facility.

2. The system according to claim 1, wherein said filter packages comprise a combination of at least one woven stainless steel wire mesh, an inert polyurethane core, an activated carbon core, a sanitary paper core, and a duct shutter door, all arranged side by side.

3. The system according to claim 1, wherein said network is underground.

4. The system according to claim 1, wherein the collection trap is connected to a dewatering pump.

5. The system according to claim 1, wherein the main trunk network includes a turbine fan, which forces air during transportation.

* * * * *